United States Patent [19]

Pagniez et al.

[11] Patent Number: 5,260,494
[45] Date of Patent: Nov. 9, 1993

[54] PREPARATION OF SODIUM FLUOROALCOHOLATES

[75] Inventors: Guy Pagniez, Poey De Lescar; Philippe Potin, Billere, both of France

[73] Assignee: Atochem, Puteaux, France

[21] Appl. No.: 22,846

[22] Filed: Feb. 25, 1993

Related U.S. Application Data

[63] Continuation of Ser. No. 330,368, Mar. 29, 1989, abandoned.

[30] Foreign Application Priority Data

Mar. 29, 1988 [FR] France ............... 88 04086

[51] Int. Cl.⁵ .................. C07C 29/70; C07C 29/00
[52] U.S. Cl. .................................................. 568/842
[58] Field of Search ................................... 568/842

[56] References Cited

U.S. PATENT DOCUMENTS

| | | | |
|---|---|---|---|
| 3,418,383 | 12/1968 | Lenz et al. | 568/851 |
| 3,702,833 | 11/1972 | Rose et al. | 568/399 |
| 4,568,779 | 2/1986 | Sulzer et al. | 568/842 |
| 4,593,129 | 1/1986 | Wilson et al. | 568/774 |

*Primary Examiner*—Howard T. Mars
*Attorney, Agent, or Firm*—Burns, Doane, Swecker & Mathis

[57] ABSTRACT

The sodium fluoroalcoholates are prepared under conditions resulting in neither reactant nor final product degradation, by (a) reacting, under reflux, the corresponding fluoroalcohols, e.g., the mono-, di- or trifluoroethanols, with sodium methanolate in the presence of a solvent having a boiling point higher than that of methanol and/or a solvent which forms an azeotrope with methanol, and (b) selectively trapping the methanol of reaction, e.g., in a molecular sieve, as it is released into the vapors which evolve upon refluxing the step (a) reaction mixture; the sodium fluoroalcoholates thus produced are well suited for direct reaction with polydichlorophosphazenes.

8 Claims, 1 Drawing Sheet

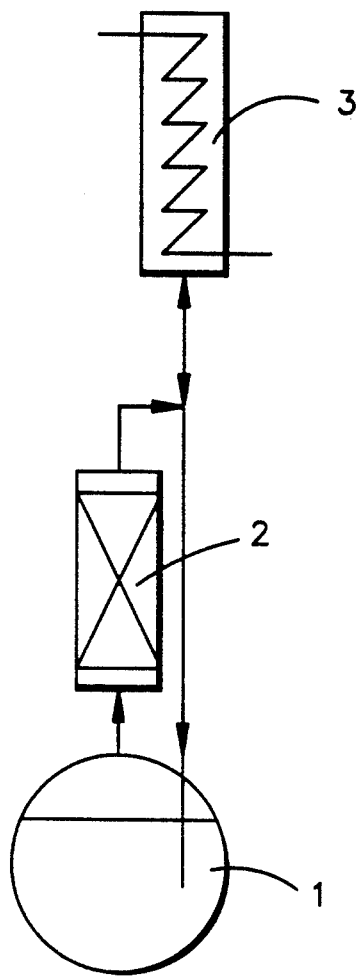
FIG. 1
FIG. 3
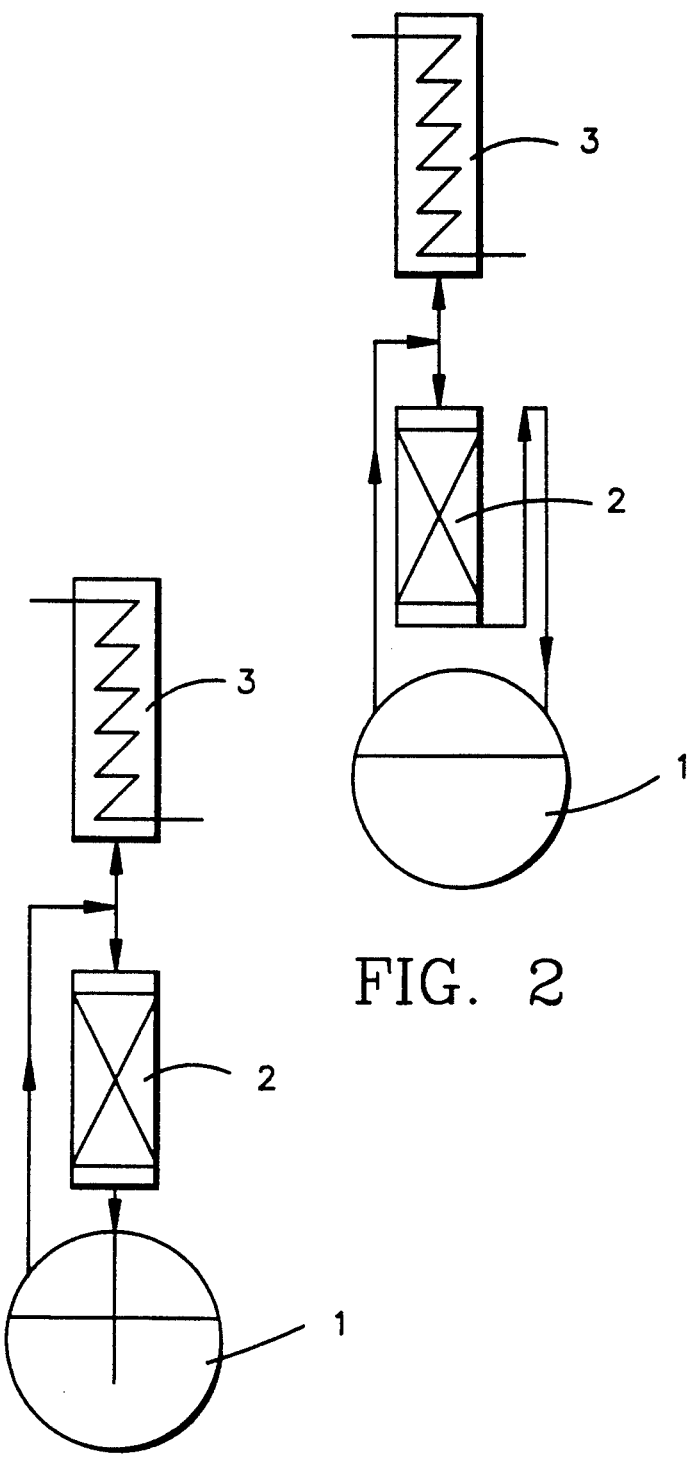
FIG. 2

PREPARATION OF SODIUM FLUOROALCOHOLATES

This application is a continuation, of application Ser. No. 07/330,368, filed Mar. 29, 1989, now abandoned.

BACKGROUND OF THE INVENTION

1. Field of the Invention

The present invention relates to an improved process for the preparation of sodium fluoroalcoholates, and, more especially, to an improved process for the preparation of sodium fluoroalcoholates by reacting the corresponding fluoroalcohols with sodium methanolate, while selectively trapping the methanol of reaction.

2. Description of the Prior Art

There are numerous applications for the sodium fluoroalcoholates which are known to this art. For example, poly(fluoroalkoxy)phosphazenes may be prepared by reacting sodium fluoroalcoholates with polydichlorophosphazene, according to the reaction scheme:

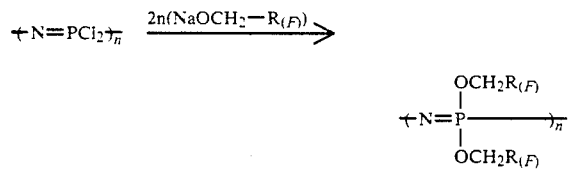

(compare, e.g., U.S. Pat. No. 3,515,688).

Various methods have been proposed to the art for preparing sodium fluoroalcoholates, by an alkalinization reaction using sodium or a sodium compound, such reaction hereinafter being designated sodionation for the sake of simplicity.

Thus, U.S. Pat. No. 3,702,833 describes the heating of fluoroalcohols with metallic sodium, under reflux, in tetrahydrofuran (THF). Depending on the particular alcohol used, this reaction entails varying degrees of degradation, resulting in the formation of sodium fluoride, and the basicity of the reaction medium is less than would be expected, considering the amount of sodium used.

U.S. Pat. No. 4,357,458 describes sodionation using sodium hydroxide, characterized by a displacement of the reaction equilibrium by distillation of a hydrocarbon which entrains the water formed during the reaction. This technique requires a long reaction time (generally greater than 20 hours).

U.S. Pat. Nos. 4,568,779 and 4,593,129 feature dispersing the sodium in finely divided form in a cycloalkane prior to contacting it with a fluoroalcohol. In this manner, the reactivity of the sodium is increased and it is thus possible to conduct the reaction at a low temperature. However, this process requires the use of a reactor which is equipped with a system for atomizing sodium, another refrigerated reactor for carrying out the sodionation, and the substitution reaction itself is carried out in yet a third apparatus.

It will be appreciated that even using atomized sodium, the reaction remains of long duration when it is carried out at low temperature.

SUMMARY OF THE INVENTION

Accordingly, a major object of the present invention is the provision of an improved process for the simple and rapid sodionation of fluoroalcohols.

Another object of this invention is the provision of an improved process for the sodionation of fluoroalcohols which entails neither reactant nor final product degradation.

Yet another object of the present invention is th provision of an improved process for the sodionation of fluoroalcohols which may be carried out in the same reaction vessel as is a downstream polydichlorophosphazene substitution reaction.

Briefly, the present invention features a process for the preparation of sodium fluoroalcoholates by (a) reacting a fluoroalcohol with sodium methanolate in the presence of a solvent having a boiling point higher than that of methanol and/or a solvent which forms an azeotrope with methanol, and (b) selectively trapping the methanol of reaction as it is released into the vapors which evolve upon refluxing the reaction mixture produced in step (a).

BRIEF DESCRIPTION OF THE DRAWINGS

FIG. 1 is a diagrammatic/schematic representation of the process/apparatus according to the present invention;

FIG. 2 is a diagrammatic/schematic representation of another embodiment of the process/apparatus according to the invention; and FIG. 3 is a diagrammatic/schematic representation of yet another embodiment of the process/apparatus according to the invention.

DETAILED DESCRIPTION OF THE PREFERRED EMBODIMENTS OF THE INVENTION

More particularly according to the present invention, by "solvent having a boiling point higher than that of methanol" is intended any solvent having this particular property, at least at a certain pressure.

The selective separation of the methanol is advantageously carried out using a molecular sieve of adequate porosity. For this purpose, it is preferable to use molecular sieves having pore diameters of about 4 Ångströms.

In a preferred embodiment of the present invention, sodium methanolate is first prepared, for example by reacting sodium with anhydrous methanol in a solvent of the above type, e.g., THF, dimethoxyethane, benzene, cyclohexane, dioxane or toluene.

In an alternate embodiment, the sodium methanolate may be prepared in an excess of methanol, which is subsequently evaporated and replaced by a solvent which can be selected from among those identified above.

A low boiling point fluoroalcohol is next introduced into the same reactor, either alone or admixed with other fluoroalcohols and/or other compounds containing labile hydrogen atoms, such as aliphatic alcohols or phenols.

The fluoroalcohols may be different compounds of the formula $R_{(F)}(CH_2)_nOH$, in which $R_{(F)}$ is a partially fluorinated or perfluorinated aliphatic hydrocarbon radical having from 1 to 12 carbon atoms, and n is equal to 1 or 0. The preferred compounds according to this invention are the mono-, di- and trifluoroethanols.

The reaction mixture thus obtained is heated to reflux.

The vapors evolved comprise methanol, fluoroalcohol and solvent. In a first embodiment of the invention, as shown in FIG. 1, these vapors ascent from the reactor 1 through a column 2 charged with a molecular sieve, for example with zeolite 4A, are condensed in condenser 3, and flow back into the reactor 1.

In a second embodiment of the invention, shown in FIG. 2, the evolved vapors are condensed directly in the condenser 3 and the condensate flows through the column 2 charged with the molecular sieve, from top to bottom, into the reactor 1, the column 2 being kept full utilizing a siphon.

In a third embodiment of the invention, shown in FIG. 3, the evolved vapors are condensed directly in the condenser 3 and the condensate flows through the column 2 charged with the molecular sieve, from top to bottom, back into the reactor 1.

In each embodiment, the molecular sieve selectively retains the methanol, with the fluoroalcohol and the solvent being recycled back into the reactor.

Completion of the reaction is easily detected by the absence of free methanol or sodium methanolate in the reaction medium.

Aside from the complete absence of degradation of the reactants and/or the products resulting from the sodionation reaction, the process according to the present invention has the unexpected advantage of permitting the sodium fluoroalcoholates thus produced to be directly used, in the same reactor, as reactants in a polydichlorophosphazene substitution reaction. In this regard, it is possible to simply introduce polydichlorophosphazene into the medium resulting from the upstream reaction, advantageously in the form of a solution in a hydrocarbon, such as a monocyclic or polycyclic aromatic hydrocarbon (benzene, naphthalene, and the like) or a mixture containing compounds of this type, and subject the mixture thus constituted to the conventional conditions for such substitution reaction.

In order to further illustrate the present invention and the advantages thereof, the following specific examples are given, it being understood that same are intended only as illustrative and in nowise limitative.

In said examples to follow, all of the operations were carried out under pressurized nitrogen, and the solvents and reactants were anhydrous. The sodium was stripped of any trace amounts of sodium hydroxide.

EXAMPLE 1

Comparative 26.22 g of trifluoroethanol (0.262 mole), 24.55 g 1,1,1'-trihydro-omega-perfluoro-1-alkanol ($HCF_2(CF_2)_{2.4}CH_2OH$) (0.122 mole), 150 g of diethylene glycol dimethyl ether and 8.03 g of sodium (0.349 gram atom) were introduced into a reactor.

The reaction medium was maintained at 60° C. The sodium thus disappeared over 2 hours. As the sodium disappeared, a copious precipitate was formed and the reaction medium darkened.

The theoretical basicity of the reaction medium should have been 0.349 equivalents. The basicity found by acidimetry was only 0.026 equivalent. 92.5% of the sodium was thus consumed by the reaction with the fluorine, which was confirmed by analysis of the precipitate.

EXAMPLE 2

Comparative 3.29 g of sodium (0.143 gram atom) were finely divided by vigorous agitation in 196 g of refluxing toluene. Into this medium, cooled to 0° C., 43.85 g of 1,1,1'-trihydro-omega-perfluoro-1-alkanol (0.217 mole) were introduced.

Between 0° and 10° C., no reaction was apparent.

Between 10° and 20° C., a weak evolution of hydrogen was observed.

The reaction medium was maintained at 25° C. for 24 hours. The entirety of the sodium disappeared and a white precipitate was formed.

Acidimetry indicated a basicity of 0.114 equivalent, instead of the expected 0.143, or a loss of 20%.

EXAMPLE 3

A solution of sodium methanolate in methanol was prepared from 180 g of methanol and 3.40 g of sodium (0.147 gram atom).

The methanol was evaporated and replaced by 300 ml of THF. To this solution was added a mixture of 9.98 g of trifluoroethanol (0.0997 mole), 9.61 g of 1,1,1'-trihydro-omega-perfluoro-1-alkanol (0.0476 mole) and 1.50 g of orthoallylphenol (0.0108 mole).

The reactor was fitted as shown in FIG. 2, the column 2 of which was filled with 140 g of molecular sieve 4A.

The reaction medium was placed under reflux. The evolved vapors thus passed through the column of molecular sieve before returning to the reactor 1. After 2 hours, no trace of methanol was detected in the reaction medium. No precipitate was observed.

Acidimetry indicated a basicity of 0.147 equivalent, representing a quantitative yield of $R_F(CH_2)ONa$.

EXAMPLE 4

A solution of sodium methanolate in methanol was prepared from 20 g of methanol and 2.135 g of sodium (0.0928 gram atom.

The methanol was evaporated off and replaced by 217.5 g of dimethoxyethane.

To this solution were added 5.545 g of trifluoroethanol (0.055 mole), 5.778 g of 1,1,1'-trihydro-omega-perfluoro-1-alkanol (0.029 mole) and 0.825 g of orthoallylphenol (0.006 mole).

The reactor 1 was fitted with a column 2 containing 65 g of sieve 4A, a reflux condenser 3 and a return conduit for the condensates back into the reactor according to the embodiment of FIG. 1.

After 2 hours under reflux, the reaction medium contained no more than 3 ppm of methanol and no trace of precipitate was observed.

Acidimetry indicated a basicity of 0.093 equivalent, or a quantitative yield of sodium fluoroalcoholates.

EXAMPLE 5 solution of alcoholates produced in Example 4 was added a solution containing 4.93 g of polydichlorophosphazene (0.085 chlorinated equivalent), 14.8 g of naphthalene and 14.8 g of benzene.

The mixture was heated at 70° C. for 12 hours.

The reaction medium was concentrated and redissolved in the minimum of THF, filtered through kieselguhr and precipitated in methanol. It was subsequently ground in methanol and dried under vacuum (temperature 60° C.); reduced pressure of 133 Pa).

In this manner, 12.46 g of rubbery polymer were prepared, a yield of 85% relative to the starting material polymer.

EXAMPLE 6

A solution of sodium methanolate in methanol was prepared from 6 g of methanol in 200 g of dimethoxyethane and 3.430 g of sodium (0.149 gram atom).

To this solution were added 8.720 g of trifluoroethanol (0.087 mole), 8.438 g of 1,1,1'-trihydro-omega-perfluoro-1-alkanol (0.042 mole) and 4.508 g of orthoallylphenol (0.033 mole).

The reactor was fitted with a column 2 containing 65 g of sieve 4A, a reflux condenser 3 and a return conduit for the condensates back into the reactor according to the embodiment of FIG. 3.

After 2 hours under reflux, the reaction medium contained no more than 6 ppm of methanol and no trace of precipitate was observed.

Acidimetry indicated a basicity of 0.150 equivalent, representing a quantitative yield.

EXAMPLE 7

To the solution of alcoholates produced in Example 6 was added a solution containing 7.83 g of polydichlorophosphazene (0.135 chlorinated equivalent), 23 g of naphthalene and 23 g of benzene.

The mixture was heated at 70° C. for 12 hours.

The reaction medium was concentrated and redissolved in THF, filtered through kieselguhr, concentrated and precipitated in methanol. It was subsequently ground in methanol and dried under vacuum, (temperature 60° C.; reduced pressure of 133 Pa).

In this manner, 19.09 g of polymer were prepared, a yield of 82%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a sodium fluoroalcoholate, comprising (a) introducing a corresponding fluoroalcohol into sodium methanolate and reacting the same, under reflux, in the presence of a solvent having a boiling point higher than that of methanol and/or a solvent which forms an azeotrope with methanol, and (b) selectively trapping the methanol of reaction as it evolves from the reaction medium under reflux.

2. A process for the preparation of a sodium fluoroalcoholate, comprising (a) reacting under reflux, a corresponding fluoroalcohol with sodium methanolate in the presence of a solvent having a boiling point higher than that of methanol and/or solvents which forms an a zeotrope with methanol, and (b) selectively trapping the methanol of reaction as it evolves from the reaction medium under reflux, in a molecular sieve.

3. The process as defined by claim 2, said molecular sieve comprising a 4A zeolite.

4. The process as defined by claim 2, said molecular sieve having a pore diameter of about 4 Å.

5. The process as defined by claim 1, said solvent comprising THF, dimethoxyethane, benzene, cyclohexane, dioxane or toluene.

6. The process as defined by claim 1, comprising reacting said fluoroalcohol with anhydrous sodium methanolate.

7. The process as defined by claim 1, said fluoroalcohol comprising a mono-, di- or trifluoroethanol.

8. The process as defined by claim 1, said reaction medium further comprising a labile hydrogen compound.

* * * * *